United States Patent
Green et al.

(10) Patent No.: US 7,239,906 B1
(45) Date of Patent: Jul. 3, 2007

(54) MAGNETIC RESONANCE IMAGING SYSTEM INCLUDING A TRANSPOLAR FIXTURE

(75) Inventors: Charles A. Green, Holbrook, NY (US); William H. Wahl, Smithtown, NY (US); Arto Cinoglu, Mellville, NY (US); Keith Nickel, Mellville, NY (US); Mark Gelbien, Levittown, NY (US)

(73) Assignee: Fonar Corporation, Melville, NY (US)

( * ) Notice: Subject to any disclaimer, the term of this patent is extended or adjusted under 35 U.S.C. 154(b) by 560 days.

(21) Appl. No.: 10/126,015

(22) Filed: Apr. 18, 2002

(51) Int. Cl.
*A61B 5/055* (2006.01)

(52) U.S. Cl. .......................... 600/407; 600/410; 600/415; 324/309; 324/318; 5/601; 5/620; 5/621

(58) Field of Classification Search .............. 600/415, 600/407, 410, 425; 324/318, 307, 309, 322; 378/208, 209, 68; 211/105.1, 105.3, 105.4; 5/601, 613, 614, 620, 621
See application file for complete search history.

(56) References Cited

U.S. PATENT DOCUMENTS

| | | | |
|---|---|---|---|
| 4,534,358 A | 8/1985 | Young | |
| 4,771,785 A * | 9/1988 | Duer | .......................... 600/415 |
| 4,824,302 A * | 4/1989 | Schultheis et al. | .......... 410/151 |
| 5,008,624 A | 4/1991 | Yoshida | |
| 5,018,918 A * | 5/1991 | Jacobs et al. | ................ 410/145 |
| 5,042,487 A * | 8/1991 | Marquardt | ................... 600/425 |
| 5,153,546 A | 10/1992 | Laskaris | |
| 5,155,758 A | 10/1992 | Vogl | |
| 5,305,365 A | 4/1994 | Coe | |
| 5,349,956 A | 9/1994 | Bonutti | |
| 5,386,447 A | 1/1995 | Siczek | |
| 5,436,607 A | 7/1995 | Chari et al. | |
| 5,520,181 A | 5/1996 | Kreidler et al. | |
| 5,640,958 A | 6/1997 | Bonutti | |
| 5,680,861 A * | 10/1997 | Rohling | ...................... 600/407 |
| 5,735,278 A | 4/1998 | Hoult et al. | |
| 5,743,264 A | 4/1998 | Bonutti | |
| 5,779,637 A | 7/1998 | Palkovich et al. | |
| 5,983,424 A | 11/1999 | Naslund | |
| 6,212,251 B1 * | 4/2001 | Tomura et al. | ................ 378/15 |
| 6,246,239 B1 | 6/2001 | Krogmann et al. | |
| 6,385,481 B2 * | 5/2002 | Nose et al. | ..................... 600/415 |
| 6,404,202 B1 | 6/2002 | Damadian et al. | |
| 6,414,490 B1 | 7/2002 | Damadian et al. | |
| 6,465,075 B2 | 10/2002 | Kobayashi et al. | |
| 6,504,371 B1 | 1/2003 | Damadian et al. | |
| 6,776,527 B1 * | 8/2004 | Tybinkowski et al. | ...... 378/209 |
| 2001/0007588 A1 * | 7/2001 | Iizuka | ........................ 378/209 |
| 2001/0029330 A1 | 10/2001 | Nose et al. | |
| 2002/0013524 A1 | 1/2002 | Hayashi et al. | |
| 2003/0204136 A1 * | 10/2003 | Green et al. | ................. 600/415 |
| 2004/0030241 A1 * | 2/2004 | Green et al. | ................. 600/422 |

* cited by examiner

FOREIGN PATENT DOCUMENTS

JP        1-242056        9/1989

OTHER PUBLICATIONS

U.S. Appl. No. 09/718,946.

*Primary Examiner*—Ruth S. Smith
(74) *Attorney, Agent, or Firm*—Lerner, David, Littenberg, Krumholz & Mentlik, LLP

(57) ABSTRACT

A magnetic resonance imaging system is provided with a fixture which can be mounted to the static field magnet within the patient-receiving space of the magnet. The fixture can support and stabilize the patient.

14 Claims, 8 Drawing Sheets

MAGNETIC RESONANCE IMAGING SYSTEM INCLUDING A TRANSPOLAR FIXTURE

BACKGROUND OF THE INVENTION

The present invention relates to imaging techniques and apparatus for performing such techniques, and more specifically to techniques and apparatuses for assisting patient positioning while performing such imaging techniques are performed.

In magnetic resonance imaging ("MRI"), a strong, uniform magnetic field is applied to the region of the patient to be imaged. Radio frequency ("RF") energy is applied to this region of the patient by a transmitter and antenna. The RF energy excites atomic nuclei within the patient's tissues. The excited nuclei spin at a rate dependent upon the magnetic field. As they spin, they emit faint RF signals, referred to herein as magnetic resonance signals. By applying small magnetic field gradients so that the magnitude of the magnetic field varies with location within the patient's body, the magnetic resonance phenomenon can be limited to only a particular region or "slice" of the patient's body, so that all of the magnetic resonance signals come from that slice. Moreover, by applying additional magnetic field gradients, the frequency and phase of the magnetic resonance signals from different locations within the slice can be made to vary in a predictable manner depending upon the position within the slice. Stated another way, the magnetic resonance signals are "spatially encoded," so that it is possible to distinguish between signals from different parts of a slice.

If this process is repeated numerous times to elicit signals using different gradients, it is possible to derive a set of information which indicates one or more characteristics of magnetic resonance signals from particular locations within the patient's body. Such a set of information is referred herein to as an image data set. Because the characteristics of the magnetic resonance signals vary with the concentration of different chemical substances and other chemical characteristics of the tissues, different tissues provide different magnetic resonance signal characteristics. When a magnetic resonance signal image data set is displayed in a visual format, such as on a computer screen or printed image, the information forms a picture of the structures within the patient's body, with different tissues having different intensities or colors.

Typically, a magnetic resonance image data set is stored as a set of individual data elements. The data in each element represents one or more characteristics of magnetic resonance signals from a small volume element or "voxel." For example, the map can be stored as a three-dimensional array of data elements, the dimensions of the array corresponding to three-dimensional space. Data elements corresponding to a given plane in three-dimensional space can be selected for display in a two-dimensional picture such as a screen display or printed image. Each small area element on the surface of the picture, commonly referred to as a "pixel," is assigned an intensity or color value based on the numerical values of the data element for the corresponding voxel.

MRI has been widely adopted in the medical arts. Because MRI does not use X-rays or other ionizing radiation, it offers safety advantages over techniques such as conventional X-ray imaging, fluoroscopy and CAT imaging. Moreover, MRI allows visualization of tissues which are difficult or impossible to depict using other techniques. Magnetic resonance imaging can show abnormal tissues in contrast to surrounding normal tissues. MRI is also particularly useful in imaging the spine. MRI can depict the vertebrae in conjunction with related tissues such as the lamina or "discs," as well as nerves, muscles and other neighboring tissues.

However, magnetic resonance imaging procedures have suffered from significant limitations. Conventional MRI equipment requires the patient to lie in a supine position on a horizontal bed which fits with the patient-receiving space of the static field magnet. Some medical conditions have effects which change with posture. For example, a spinal disc may impinge on a nerve or other surrounding structure only when the patient is in an upright posture so that the disk is compressed by the patient's weight. Various proposals have been advanced to allow MRI procedures to be performed on patients in a posture other than the conventional supplying of posture. For example, Japanese published Patent Application No. 1-242056 published Sep. 27, 1989 depicts a magnetic resonance imaging unit with a tilting bed for supporting the patient in a supine position or in a standing position. Yoshida, U.S. Pat. No. 5,008,624 depicts a magnetic resonance imaging instrument with movable static field magnet in conjunction with a patient carrier which supports the patient in "various postures." Palkovich et al., U.S. Pat. No. 5,779,637 discloses a system in which the patient lies supine within the static field magnet during one imaging procedure. The entire system, including the static field magnet and the patient can be pivoted so as to swing the magnet, the patient bed and the patient as a unit to a different position in which the patient bed extends vertically and the patient in an upright posture. A further image is taken in this position. None of these systems have been widely adopted.

Copending, commonly assigned U.S. patent application Ser. No. 09/718,946, filed Nov. 22, 2000 ("the '946 application"), the disclosure of which is hereby incorporated by reference herein and copending commonly assigned U.S. patent application Ser. No. 09/789,460 ("the '460 application") the disclosure of which is also incorporated by reference herein describe additional MRI magnet structures and patient handling devices as well as additional imaging methods. As disclosed for example in certain embodiments of the '946 application, a patient support such as a bed which can both tilt and elevate can be used in conjunction with a static field magnet to allow imaging of a patient in various orientations and to position various portions of the patient's anatomy in the appropriate location relative to the magnet for imaging. Discussion of the '946 and '460 applications in this background section of the present application should not be taken as an admission that the same constitute legally available prior art with respect to the present invention.

The patient support system including the bed and the tilt and elevate mechanisms disclosed in the '946 application can place a patient in positions from which a patient may have a fear of slipping or falling, regardless of whether that fear is justified. For example, a standing patient's longitudinal axis is substantially vertical, the patient may have a fear that he or she will fall away from the bed. The patient may be stabilized, supported or restrained to prevent the patient from falling off the bed, or to give the patient further reassurance. While it is possible to restrain the patient by strapping the patient to the bed, this may be inconvenient and may be physically uncomfortable or disturbing to the patient. For example, one desirable implementation of the system disclosed in the '946 application is a "walk-in" imaging procedure in which a patient can walk onto a footrest associated with the bed, step onto the footrest and lean against the bed as the bed moves and elevates. A significant advantage of this procedure is that it is convenient and psychologically non-threatening to the patient. If the patient has to be strapped to the bed, this advantage is reduced.

SUMMARY OF THE INVENTION

One aspect of the present invention provides a fixture for a magnetic resonance imaging apparatus having a first pole face and an opposed second pole face. The fixture according to this aspect of the present invention desirably includes a support structure and first and second pads connected to the support structure. The first and second pads are movable relative to one another between a collapsed condition in which said pads are disposed at a first distance from one another, and an expanded condition in which the pads are at a second distance from one another greater than the first distance. The first and second pads engage the first and second pole faces of the imaging apparatus when the support structure is disposed between the pole faces and the first and second pads are in the expanded condition. The pads will then secure the support structure to the pole faces when the pads are in the expanded condition.

In particularly preferred arrangements, the first and second pads are arranged to bear on the pole faces and frictionally engage the pole faces. This allows the fixture to be positioned anywhere on the pole faces, and in any position relative to the patient bed. Moreover, the preferred fixtures according to this aspect of the invention do not require modifications to the magnetic resonance imaging apparatus or the patient support. Most preferably, the fixture is substantially in the form of an elongated rod when the pads are in the expanded position. Such a fixture can be positioned, for example, in front of a standing or seated patient. The patient can grasp the support structure for reassurance against falling. At least with ambulatory, conscious patients having some physical ability, the use of a fixture in accordance with this aspect of the present invention can avoid the need to strap the patient to the bed. Moreover, such a fixture can be positioned as needed to support parts of the patient's body in desired positions for imaging.

A further aspect of the present invention provides a combination of magnetic resonance imaging apparatus including a static field magnet, a patient support and a fixture, which may be a fixture as described above or another form of fixture affixed to the static field magnet. The magnetic resonance imaging apparatus has opposed first and second pole faces spaced apart from one another and define a patient-receiving space. The patient support supports a patient or equipment within the patient-receiving space.

A further aspect of the present invention provides methods of magnetic resonance imaging. Methods according to this aspect of the invention desirably include the steps of loading a patient onto a patient support system of a magnetic resonance imaging apparatus and positioning the patient support system such that at least a part of the patient is disposed in a patient-receiving space between pole faces of a static field magnet in the magnetic resonance imaging system. Most preferably, the method further includes the step of providing a fixture affixed to the static field magnet extending within the patient-receiving space. The patient can engage the fixture. Alternatively, or additionally, the fixture can support an MRI imaging coil or other equipment used with the patient-receiving space.

DETAILED DESCRIPTION OF THE PREFERRED EMBODIMENTS

Figure 1:
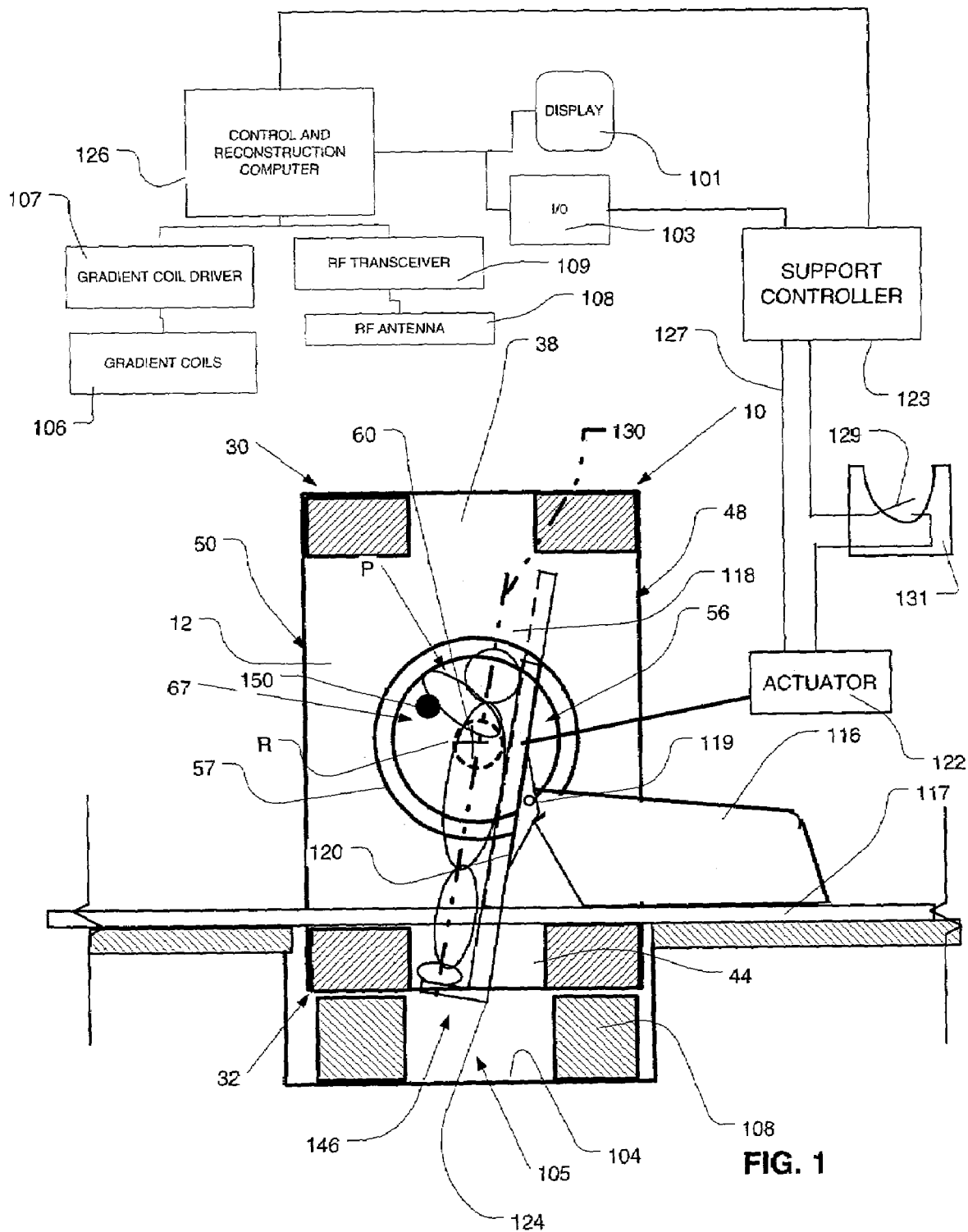
FIG. 1 is a diagrammatic sectional view of one apparatus incorporating a fixture in accordance with one embodiment of the invention for which the current invention is designed.

Apparatus according to one embodiment of the present invention includes a ferromagnetic frame 10. As described in greater detail in the '946 application, the frame 10 is generally box-like and includes a top flux return member 30 defining the top wall of the box, a bottom flux return member 32 defining the bottom wall of the box and a pair of generally vertical side walls 12 and 13 (FIG. 2) defining the sides of the box, one such side wall 12 being visible in FIG. 1. The box-like structure has large patient entry openings 48 and 50 (FIG. 1) at front and back sides of the box, i.e., the vertical sides which are not occupied by side wall 12 and the opposite side wall. The top flux return member 30 defines opening 38 in the top wall of the box, whereas the bottom flux return member 32 defines an opening 44 in the bottom wall. The box-like structure is maintained above a base structure 104 so that there is a space 105 beneath the bottom of the flux return member communicating with opening 44.

Two cylindrical ferromagnetic poles 56, extend into the box from side walls 12 and 13. The poles extend on a common horizontal polar axis 60 and define a patient-receiving space 67 between them. The apparatus also includes a source of magnetic flux such as electromagnet coils 57 encircling the poles for providing a constant, substantially uniform static magnetic field within patient-receiving space 67.

A patient support system 146 having a carriage 116 has a patient positioning assembly mounted thereon. The patient positioning assembly includes an elongated elevator frame pivotally mounted to the carriage for movement about a horizontal pivot axis 119. The patient positioning assembly further includes an elongated patient support or bed 120 with a footrest 124 at one end. The patient support is slidably mounted on the carriage. An actuator assembly 122 is provided for driving the carriage along rails 117; for moving the patient support along the elevator frame 118 and for tilting the elevator frame about axis 119 relative to the carriage. Actuator assembly may include any devices which can be used to impel mechanical elements relative to one another in a controllable manner. For example, the actuator assembly can incorporate one or more motion sources such as rotary or linear electric motors, pneumatic or hydraulic motors, pneumatic or hydraulic cylinders and the like, and may also include mechanical linkages such as gears, belts, screws, racks, levers, chains, ropes and pulleys connecting each motion source between one or more pairs of elements. The actuator typically also includes control elements such as clutches, switches, valves and brakes responsive to externally-applied control signals. Additionally, the actuator assembly desirably includes feedback elements such as optical or electronic position encoders, switches or mechanical linkages. One set of feedback elements is linked to elevator frame 118 and patient support 120 for providing signals indicative of the position of the patient support relative to the elevator frame, whereas a further set of feedback elements is linked to elevator frame 118 and carriage 116 for providing signals indicative of the angular position of the elevator frame relative to the carriage. Yet another set of feedback elements provides an indication as to the position of carriage 116 on rails 117. The feedback elements can be directly linked to the elevator frame, patient support and carriage, or else can be indirectly connected to these elements through intermediate linkages as, for example, through linkages used to transmit motion from the motion source. The individual elements of the actuator assembly can be conventional elements as generally employed in automatic machinery. Those portions of the actuator assembly, carriage and patient support which extend within the patient-receiving space 67 during operation desirably are formed from non-magnetic materials and do not emit magnetic fields during operation. The carriage 116 is moveable on rails 117 extending into and out of magnetic frame through the patient entry openings 48 and 50.

A set of gradient coils 106 is physically mounted within the magnet frame. The gradient coils are arranged in the conventional manner to apply magnetic field gradients within the patient-receiving space. The gradient coils in turn are connected to a gradient coil driver 107 which is controlled by computer 126. In the conventional manner, the computer 126 can control the gradient coil driver to apply appropriate currents to the various gradient coils so as to provide gradients in the desired direction within patient-receiving space 67 and to vary these gradients with time.

Figure 2:
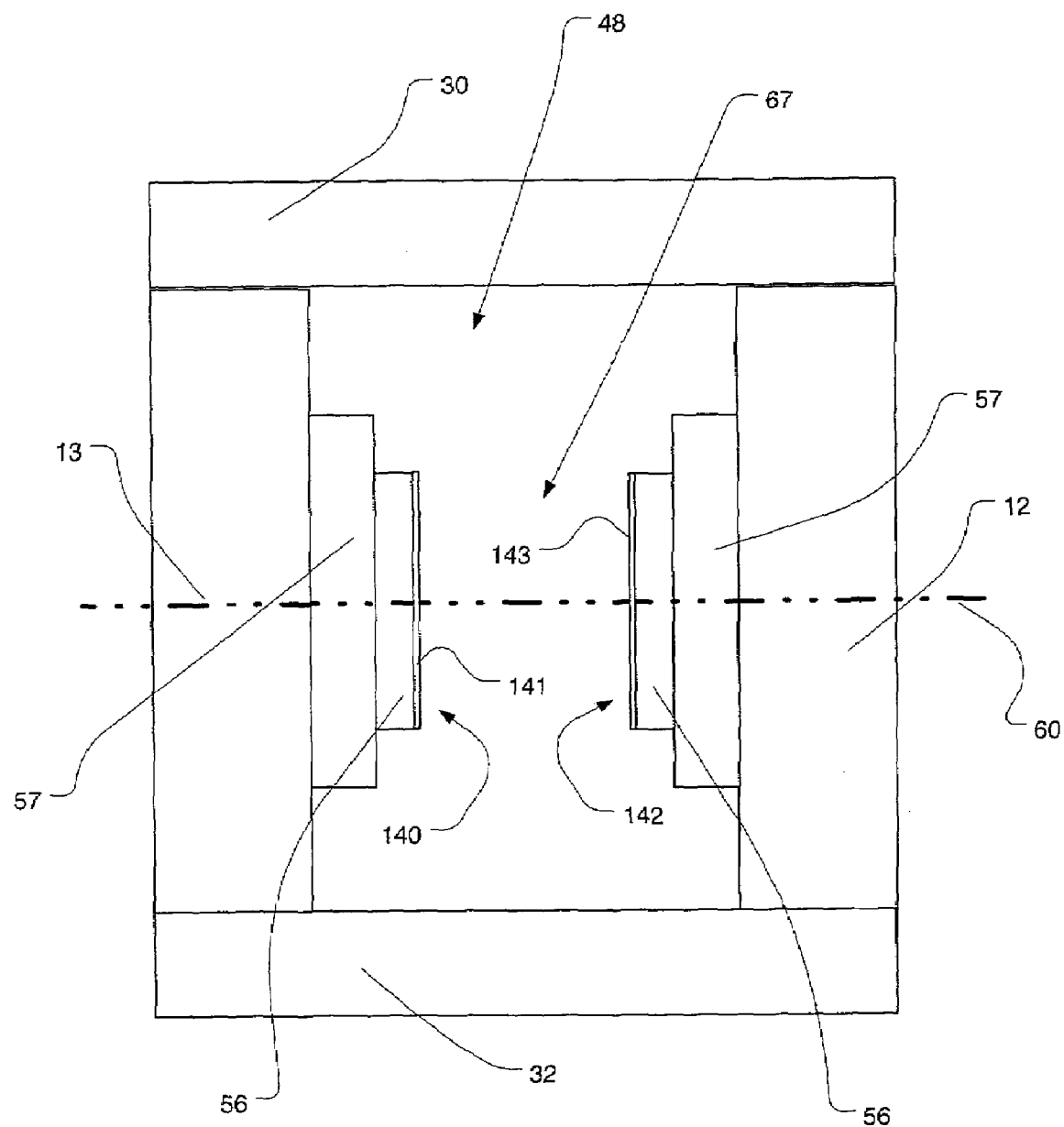
FIG. 2 is a diagrammatic end elevational view depicting part of the apparatus shown in FIG. 1.

As best seen in FIG. 2, magnetic poles 56 define opposed pole surfaces 140 and a second surface 142 (FIG. 2). Typically, the poles 56 include pole cap structures 141 and 143 which define the exposed pole surfaces 140 and 142. These pole cap structures are fixed to the remainder of the poles. The pole cap structures may include ferromagnetic elements such as ferromagnetic shim rings, and also may include non-ferromagnetic structures such as some or all of the gradient coils 106 (FIG. 1). Typically, the gradient coils are "potted" or encapsulated in a mass of epoxy or other resin which also forms part of the pole cap. The pole cap may also include non-functional elements such as shrouds or other structures provided to conceal the poles. As the elements of the pole cap structures are fixed in position on the remainder of the poles 56, the pole cap structures are considered as parts of the poles themselves as referred to in the present disclosure. A conventional RF antenna 108 and RF transmitting and receiving apparatus 109 are also associated with the control and reconstruction computer 126. The antenna may include one or more elements positioned in the conventional manner within the magnetic frame, on the patient support 120 or even carried by the patient. The transmitting and receiving apparatus can be actuated by the computer to apply RF excitation signals and to receive the magnetic resonance signals emitted by the patient. The apparatus may use the same or different antenna elements for transmitting and receiving.

The apparatus further includes a system controller, also referred to as a control and reconstruction computer 126, linked to a display 101 such as a CRT display or printer and input/output devices 103 for entry of data and control commands into the computer. The control and reconstruction computer includes the conventional elements of a general-purpose computer, including a programmable processor and conventional memory devices for storing data and programs. The input/output devices 103 may include conventional elements such as a keyboard, as well as a conventional pointing device such as a mouse, touchpad or trackball, and preferably also include specialized command entry devices such as switches or pushbuttons used to control at least some aspects of the patient movement as discussed below. As disclosed in commonly assigned U.S. Provisional Patent Application No. 60/332,103, filed Nov. 21, 2001 and entitled STAND-UP PATIENT HANDLING SYSTEM CONTROL KIOSK, the disclosure of which is incorporated by reference herein, it is desirable to place at least some of the devices which control movement of the patient support on a panel close to the static field magnet but spaced from the magnet so that an operator positioned at the control panel can see into the magnet and observe the patient. For example, such a panel can include a "deadman switch," i.e., a button or other element which must be held continually by the operator to enable movement of the patient support.

Actuator assembly 122 is connected to a support controller 123, which in turn is connected to system controller 126. The support controller is connected to the feedback elements of the actuator through a connection 129. The support controller is linked to the control elements of the actuator through a safety switch 129, so that the support controller only supplies power to the control elements of actuator 122 to move the patient support 120 when safety switch 129 is closed, and so that the actuator is disabled when the safety switch is open. The safety switch is mounted to a cradle 131 which is disposed outside of the patient-receiving space of the magnet and which is adapted to receive the fixture 150 discussed below. Where a control kiosk is provided, the cradle can be physically mounted on the kiosk.

As further discussed below, the support controller is arranged to receive a command directing the support controller to bring the patient support to a first disposition, and to respond to such command by operating the actuator assembly 120 to drive the carriage relative to rails 117, to move patient support relative to support frame 118, and to pivot the support frame about axis 119 relative to the carriage 116, until the feedback elements of the actuator assembly indicate that the patient support is in the first disposition, and to repeat these operations in response to a further command to bring the patient support to a different selected disposition. The support controller may include conventional control elements capable of controlling fixed sequences of operations as, for example, conventional "hard-wired" electrical control apparatus, fluidic, mechanical or electromechanical control devices. Preferably, however, the support controller includes a general-purpose computer with conventional interface devices. For example, where the motion sources included in the actuator include electrical stepper motors, the support controller includes conventional stepper motor interface elements capable of providing electrical power to the stepper motors in response to commands from the processor in the computer. The interface devices in the support controller desirably also include conventional interfaces for receiving signals from the feedback devices in the actuator assembly. The support controller is depicted in FIG. 1 as a structure separate from the control and reconstruction computer 126 but operatively connected to the control and reconstruction computer. In this case, the support controller 123 and the system controller 126 desirably also includes interfaces permitting communication between these two controllers. Alternatively, the support controller 123 may be an integral part of the system controller 126. For example, the processor of the system computer may perform the logic functions of the system controller. In either case, the support controller 123 desirably also has direct connections to at least some of the input devices 103 as, for example, to a deadman's switch as mentioned above, so that the operator can manually interrupt any movement of the patient support in an emergency. Alternatively or additionally, some of the input devices 103 may be directly connected to elements of the actuator 122. For example, a deadman's switch can be arranged to interrupt power to the actuator so as to stop movement of the patient support in an emergency regardless of any action taken by the support controller 123.

A fixture 150 (FIG. 3) in accordance with one embodiment of the present invention includes a support structure having a structural element 151. Structural element 151 incorporates a first elongated section 154 having an axis of elongation 155, and a second elongated section 156 having an axis of elongation 157. One end of section 154 is engaged in an end of section 156, and sections 154 and 156 are connected to one another by a hinge pin 152 passing through these ends so that the sections can pivot relative to one another about a hinge pivot axis 153 between an unfolded condition, seen in solid lines in FIG. 3 and a folded condition depicted in broken lines. The engaged ends of sections 154 and 156 form a stop which prevents pivoting movement beyond the unfolded condition. In the unfolded condition, sections 154 and 156 are substantially collinear, so that the included angle A between their axes of elongation 155 and 157 is approximately 180°, preferably between 175° and 185° and most preferably between 180° and 185°. Thus, in the unfolded condition the two sections 154 and 156 of the structural element 151 cooperatively form a substantially straight, elongated rod. In the folded condition, sections 154 and 156 are not collinear; the included angle A' between axes of elongation 155 and 157 is substantially less than 180°. The engaged ends of the sections desirably limit the folding movement, so that in the folded condition the included angle A' cannot be less than a predetermined minimum.

A selectively operable latch is provided for locking sections 154 and 156 in the unfolded condition. The latch includes a tubular sleeve 149 mounted on first section 154 and slidable from the unlatched condition depicted in FIG. 3 to a latched condition in which the sleeve extends over the engaged ends of the sections and surrounds hinge pin 152. A stop 147 is provided for holding the latch in the engaged position. Other forms of latches may be used as, for example, a conventional spring-loaded detent (not shown) mounted on one of the sections and arranged to engage a recess on the other section. Also, other selectively-operable mechanical devices such as clamps or bolts can be employed.

A first pad 158 is connected by a pin 162 to a threaded rod 166, which in turn is threadedly engaged in the end of the first section 154 remote from hinge 153. Thus, the first pad 158 is connected to the first section 154 so that the pad can pivot about the axis of hinge pin 162 and so that the pad can be adjusted in the direction of elongation of the first element. A second pad 160 is connected to the end of second section 156 by a pin 164 so that the second pad can pivot about the axis of pin 164. Pads 158 and 160 have engagement surfaces 159 and 161 facing outwardly, away from the structural element 151.

At least those portions of the pads constituting the engagement surfaces 159 and 161 are composed of a material having a relatively high coefficient of friction as, for example, a rubber or polyurethane composition. The structural element 151 and associated components such as the threaded rod 166 and pins should be formed from non-ferromagnetic materials such as aluminum, polymers or wood, so that they do not interfere with magnetic field uniformity during operation of the apparatus. For example, a glass-fiber reinforced polymer of the type sold under the designation G10 can be used.

Figure 3:
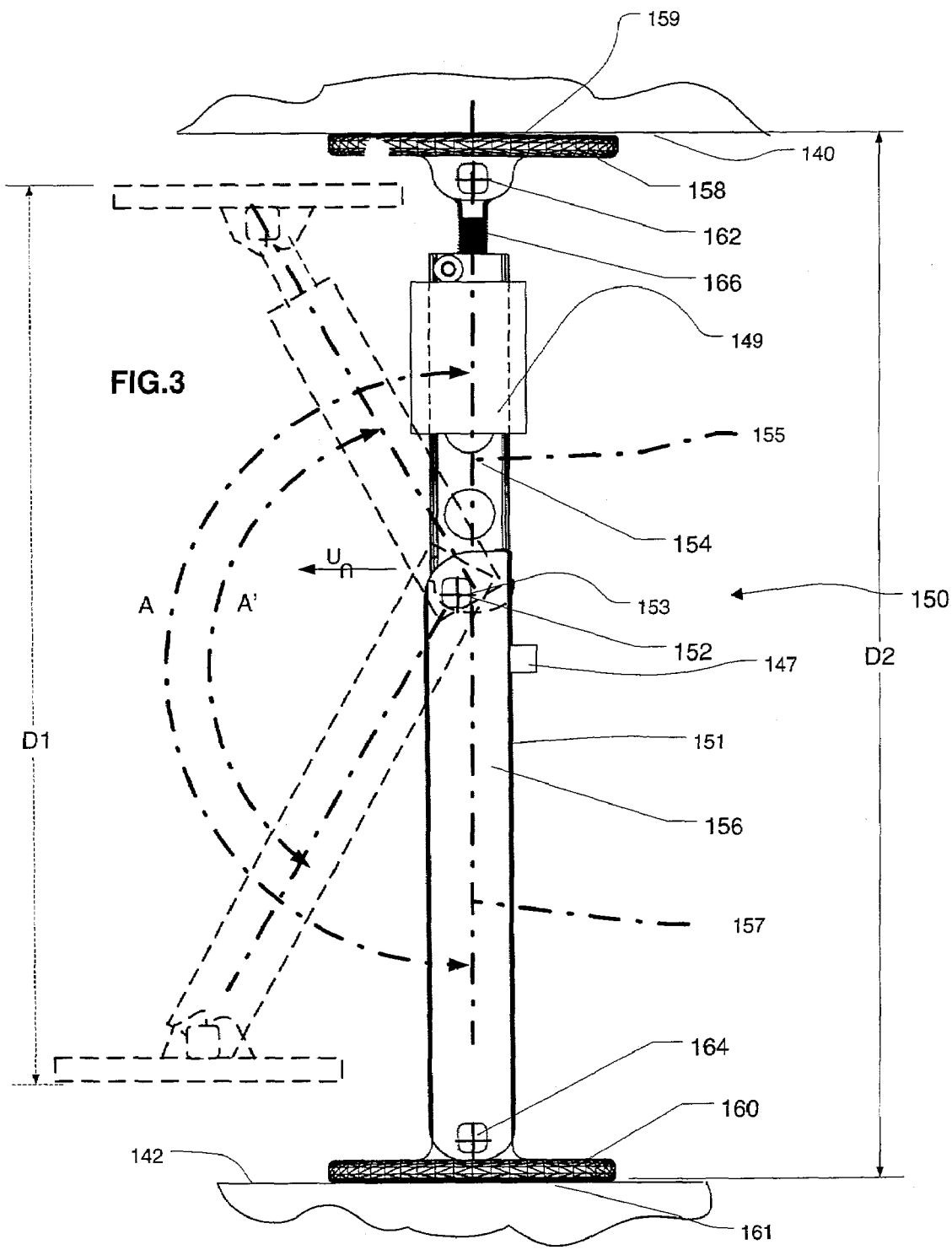
FIG. 3 is a diagrammatic plan view of the fixture of FIG. 1.

As shown in FIG. 3, when the sections 154 and 156 of the structural element 151 are in the folded condition depicted in broken lines, the pads 158 and 160 are in a collapsed condition in which the pads are disposed at a first distance $D_1$ from one another. When the sections 154 and 156 are in the unfolded condition shown in solid lines in FIG. 3, the pads are in an expanded condition in which the pads are disposed at a second distance $D_2$ from one another, this distance being greater than the first distance $D_1$. The second distance $D_2$ is selected so that it is just slightly greater than the distance between the pole faces 140 and 142. Thus, the patient support can be positioned between the pole faces 140 and 142 of the magnet by placing the support within the patient-receiving space 67 of the magnet while the sections 154 and 156 of the structural element are in the folded condition and the pads are in the collapsed condition, and then pivoting the sections to the unfolded condition so as to bring the pads 158 and 160 to the expanded condition and forcibly engage the pads with the pole faces 140 and 142. This forcibly engages the engagement surfaces 159 and 161 of the pads 158 and 160 with pole faces 140 and 142, and places the structural element 151 in compression. The force of engagement between the pads and the pole surfaces desirably is several hundred pounds or more, so as to provide frictional forces between the pads and pole faces of similar magnitudes to hold the fixture in position and resist displacement transverse to the axis of the fixture. Such forces are readily achievable because the pivoting sections 154 and 156 of the structural element act as a toggle mechanism to provide a substantial mechanical advantage. Thus, as the pads approach the fully expanded condition and begin to engage the pole faces, the operator placing the device can grasp one or both of the sections adjacent the hinge pin 153, and urge such section or sections in the unfolding direction indicated by arrow U in FIG. 3. In this condition, a small force exerted by the operator produces a large outward force urging the pads into engagement with the pole faces. If the included angle A between the sections in the unfolded condition is slightly more than 180°, the pivoting sections will go "over center" slightly, so that the compressive force exerted by the pole faces on the pads tends to hold the sections in the unfolded condition. The patient support as a whole has enough resilience to allow positioning. Typically, most of the resilience in the patient support is provided by compressibility of the pads 158 and 160. Also, pivoting of the pads relative to the sections of the structural elements, about pins 162 and 164, facilitates seating of the pads against the pole faces.

Once the sections have been brought to the unfolded condition, the operator can advance the lock 149 to the locked position so that the lock holds the sections in the unfolded condition as well, leaving the patient support securely positioned between the pole faces.

In a method according to one embodiment of the invention, the fixture 150 is initially positioned in cradle 131, so that the fixture is in an inactive position, outside of the patient-receiving space of the magnet. In this inactive position, the fixture holds safety switch 129 closed, so that the support controller 123 can command actuator 122 to move patient support 120. Also, in this inactive position, the fixture does not obstruct entry or exit of the patient.

Patient P is disposed on patient support 120 so that the patient's back rests against the support and the patient's feet rest on footrest 124. To facilitate loading, the support controller 123 may command the actuator to move the patient support to a pre-selected loading position (not shown) in which the patient support is generally vertical with footrest 124 near the level of the surrounding floor and rails 117, so that the patient can readily walk across the floor and step onto the footrest. This provides an easy and non-threatening loading procedure for ambulatory patients. Preferably, in the loading position the patient support is tilted back so that the plane of the support is at an angle of about 5–10 degrees from vertical. Thus, when the patient is positioned on the support, gravity will tend to hold the patient's back against the support. Alternatively, if the patient is somewhat debilitated, but is nonetheless able to stand, the support controller may command the actuator to move the patient support to a substantially horizontal position, so that the patient can be transferred readily onto the support from a bed or stretcher. In the loading position, the carriage optionally may be disposed so as to position the patient support 120 outside of the magnet.

After loading, the support controller 123 commands the support 120 to move to the imaging position depicted in FIG. 1. During this movement, the fixture 150 remains in the inactive position, in cradle 131. This assures that the patient cannot be pinched between the support 120 and fixture 150 by movement of the support. After the patient support moves to the imaging position depicted in FIG. 1, the fixture is removed from cradle 131 and placed in the desired location within the patient-receiving space. The fixture 150 is forcibly engaged between the pole faces as described above so that the structural element extends within the patient-receiving space 67 with the axis of the structural element substantially parallel to the polar axis 60 of the magnet. The operator may select the position of the fixture during the positioning step so that it will be convenient for the patient to grasp the structural element of the fixture for additional assurance against falling. Alternatively, the operator may place the fixture at a location such that the patient can rest his or her arms on the fixture, as seen in FIG. 1, so as to hold his or her arms in an extended position. While the fixture is disposed within the patient-receiving space, cradle 131 is empty and hence safety switch 129 is open, so that the actuator 122 cannot move the patient support 120 and the patient cannot be pinched between the support and the fixture 150 due to movement of the support.

During use, the operator can reposition the fixture 150 as desired, by releasing lock 149 (FIG. 3) and bringing the pads to the collapsed condition, then moving the fixture and again bringing the pads to the expanded condition to re-engage them with the pole faces. The fixture 150 can be repositioned with or without moving the patient support 120. If the patient support must be moved, the operator can remove the fixture 150 and place it into cradle 131 to restore operation of actuator 122, and then reposition the fixture 150 in the patient-receiving space after support 120 has been moved.

Figure 4:
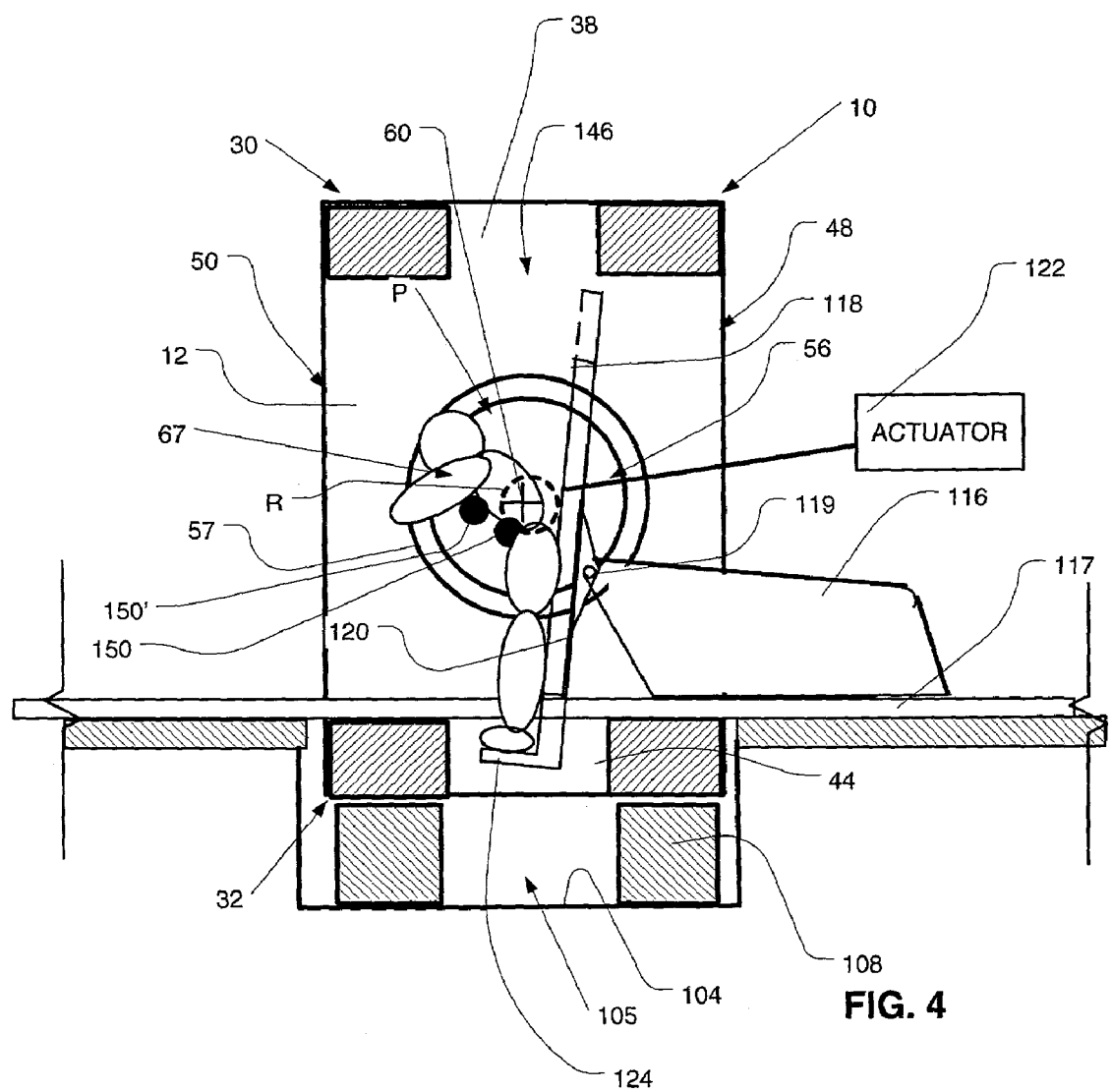
FIG. 4 is a view similar to FIG. 1, but showing the apparatus in a different operating condition.

For example, the fixture 150 can be positioned as shown in FIG. 4 so that a patient in a standing orientation can bend at the waist over fixture 150. A further fixture 150' can be engaged between the pole faces so that the patient's chest or shoulders bear against the further rest. This allows the patient to remain in a stable, forwardly-bent position during imaging. An image of the patient captured in this position can be used, for example, to diagnose orthopedic or other conditions which have effects which change with bending of the patient's body, and can reveal conditions not shown in other positions.

In similar fashion, other images can be acquired using one or more fixtures to support other portions of the patient's body as, for example to support parts of the patient's body in a specific position relative to other parts of the body. For example, in studies of the shoulder joints, it may be desirable to support a patient in a standing or seated posture with his or her arms extending forwardly at chest level. In studies of the legs, it may be desirable for the patient to hold one leg up and extended forwardly, and so on. It is generally not practical to provide specialized supports for every possible positioning need. Use of one or more fixtures in accordance with the present invention provides the versatility needed to accommodate numerous different positions in an economical and practical manner. Moreover, preferred techniques using the fixtures and magnet do not have the psychologically threatening aspects of clamping a patient into a fixture which contorts his or her body and then moving the patient in such contorted posture. For example, in the arrangement illustrated in FIG. 4, the patient support remains stationary as the patient enters the magnet and mounts the footrest 124. With the patient in a free, standing position, the support 120 and footrest 124 may be elevated or depressed slightly, but the rests 150 and 150' need not be placed in the patient-receiving space at this time. After the support and footrest are positioned, the rests 150 and 150' are positioned, whereupon the patient can lean forward voluntarily into the position shown. The patient remains free to disengage himself or herself from the rests and resume a standing posture at any time. This helps to alleviate fear.

The mechanism used for moving the pads between the collapsed position and the expanded position need not include pivoting sections of the structural element as discussed above. Thus, a fixture according to a further embodiment of the invention, schematically depicted in FIG. 5, includes an elongated, rod-like structural element 250 including a tubular housing 252 having a first end cap 254 fixed to one end. A second end cap 256 covers the opposite end of housing 252, but cap 256 is free to move relative to the housing. A threaded rod 258 is rigidly mounted within second end cap 256, and projects into housing 252. Threaded rod 258 is engaged in a threaded hole in a plate 260, which in turn is rigidly mounted within housing 252. Thus, second end cap 256 can be moved towards and away from the first end cap 254 by turning the second end cap relative to the housing and first end cap about the axis 262 of the housing.

Figure 5:
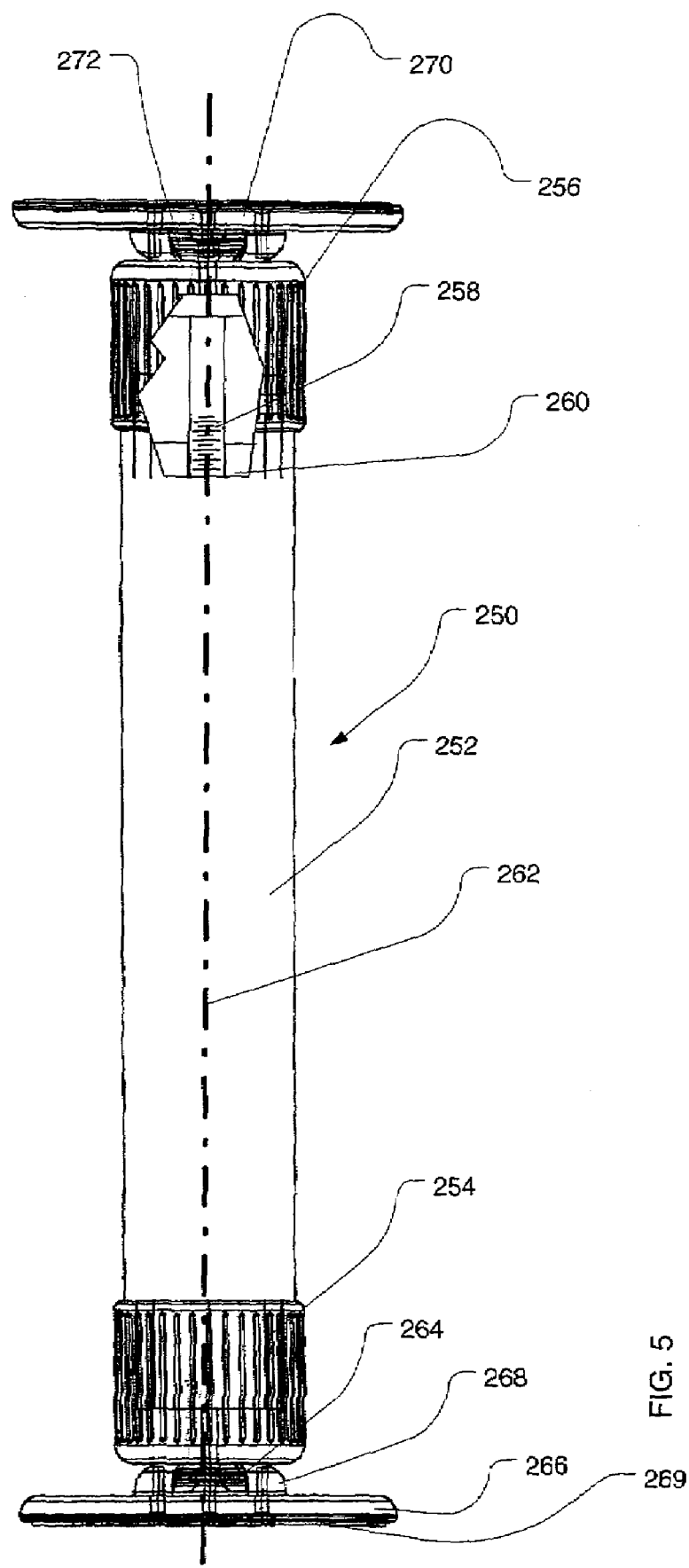
FIG. 5 is a diagrammatic elevational view of a fixture according to another embodiment of the present invention.
Figure 5A:
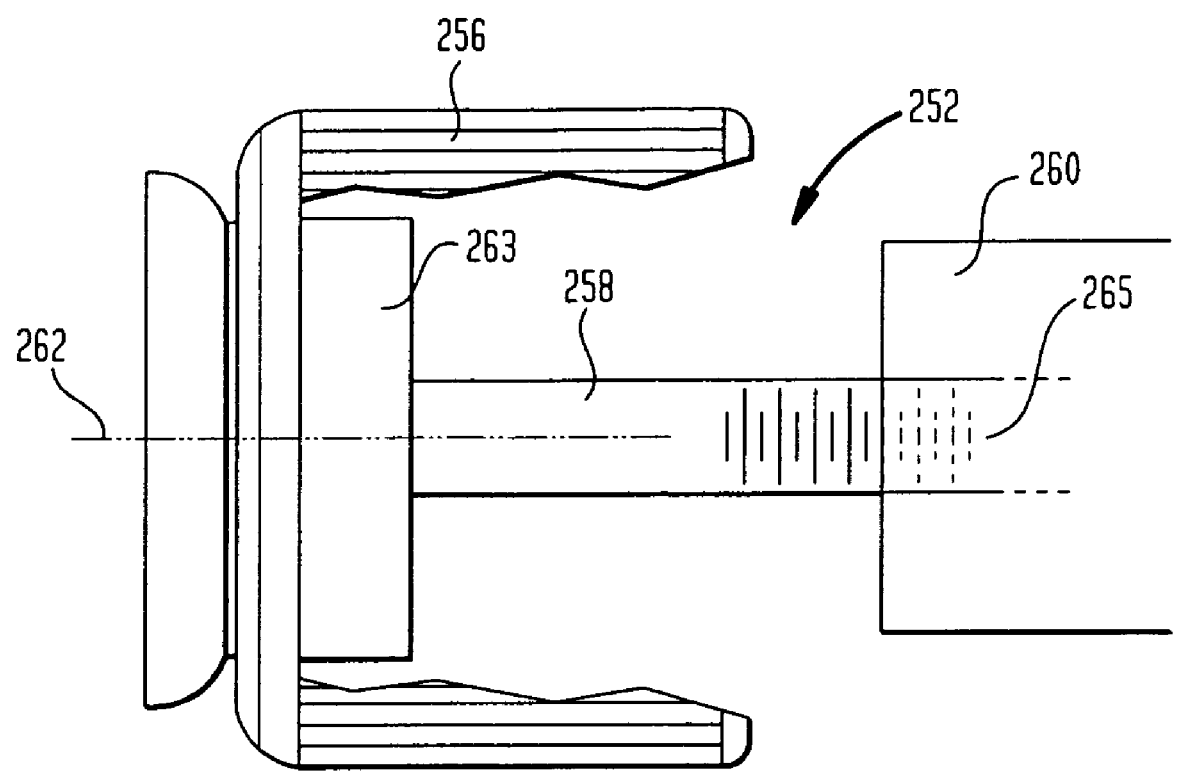
FIG. 5A is an exploded view of a portion of the fixture of FIG. 5.

In particular, and as is shown in greater detail in the exploded view of FIG. 5A, the threaded rod 258 is rigidly mounted within second end cap 256 at base member 263. The threaded rod 258 projects into housing 252 and is engaged into a threaded hole 265 in plate 260. Thus, as the second end cap 256 is turned or rotated about axis 262, the rod 258 is also turned or rotated. This rotation translates into linear movement that causes the second end cap 256 to move relative to the first end cap 254. Specifically, the second end cap 256 moves away or towards the first end cap 256 depending on the rotational direction and threading orientation. In this way, the threaded rod 258 and threaded plate 260 (via hole 265) in principle operate as a screwjack.

A bearing 264 is rigidly mounted to first end cap 254. Bearing 264 has an exterior surface in the form of a portion of a sphere. A first pad 266 is secured to the bearing by a collar 268 engaged with the exterior surface of bearing 264. This arrangement allows pad 266 to rotate relative to the first end cap about axis 262, and also allows the pad to tilt slightly about axes transverse to axis 262. The first pad has a high-friction surface such as an elastomeric layer 269 on the side facing away from the end cap and housing. A second pad 270, identical to the first pad 266, is mounted to the second end cap 258 by a similar arrangement including a bearing 272.

The rest shown in FIG. 5 can be engaged between pole surfaces by turning the end caps so that movement of the end caps forces the pads outwardly away from one another, to an expanded position. Once the pads engage the pole faces, the end caps can still be rotated to tighten the engagement. The pads can be disengaged by turning the end caps in the opposite direction, to move the pads back towards one another, to a collapsed condition.

In still other embodiments, other mechanical mechanisms, pneumatic cylinders or hydraulic cylinders can be used to move the pads relative to one another. It is not essential that the structural element of the rest include multiple sections; one pad can be fixed or pivotally mounted to a unitary structural element, whereas the opposite pad can be movable relative to such structural element. Also, it is not essential that the fixture have an elongated, rod-like structural element. For example, the structural element may be in the form of a flat platform for supporting a patient's foot or other appendage. In a further arrangement, the structural element of the patient support can include a main body provided with pads as discussed above and elements such as rings or a sling suspended from the main body, so that the patient can grasp the rings or place a limb in the sling.

A plurality of fixtures can be used in a single procedure to share the load applied by the patient, or to position a portion of the patient's body in a particular manner. Moreover, some diagnostic applications may benefit from the use of multiple fixtures 150. In an illustrative example, a patient's joint may be held in a precise position by two or more fixtures.

Figure 6:
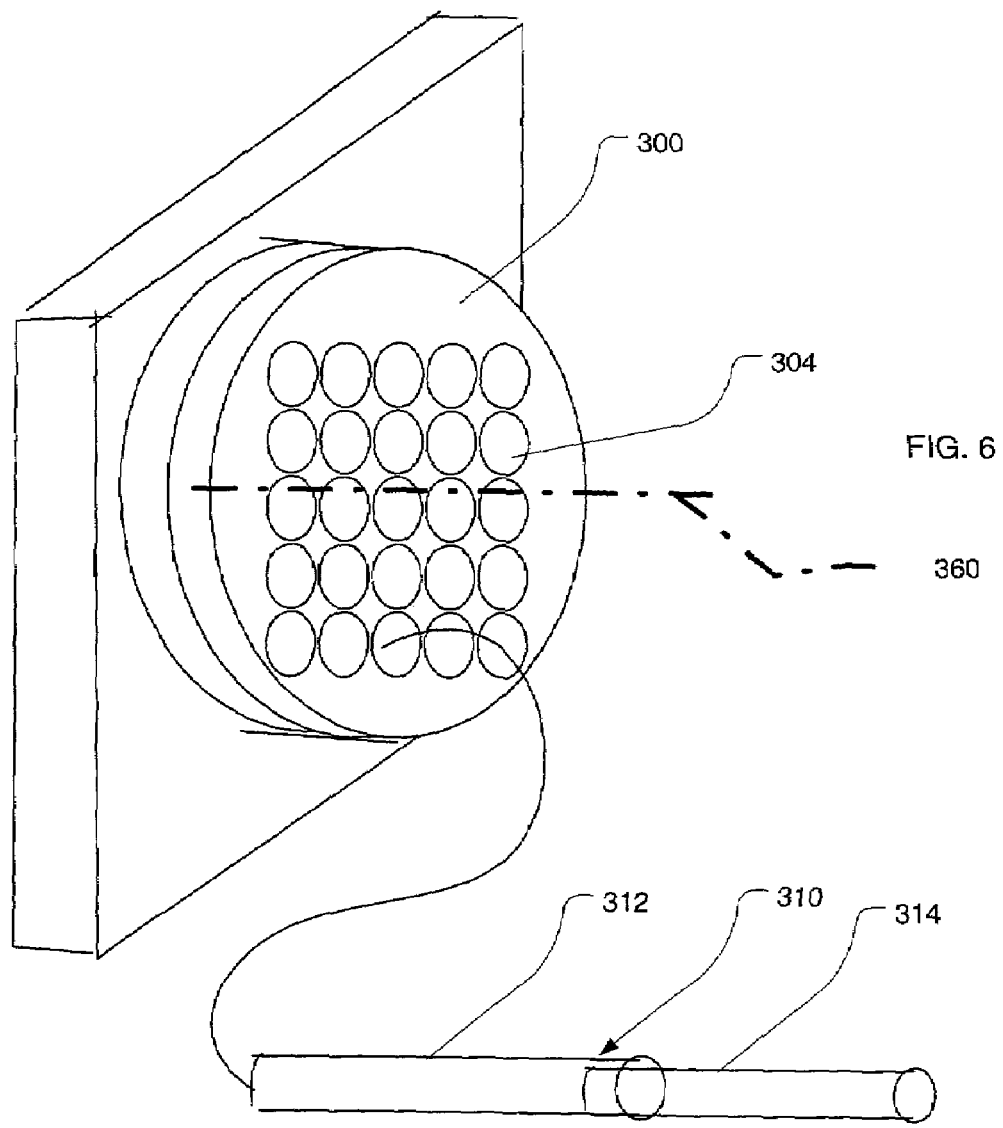
FIG. 6 is a diagrammatic perspective view depicting apparatus according to another embodiment of the invention.

In the embodiments discussed above, the pads of the fixture are frictionally engaged with the pole surfaces. This provides significant advantages in that no modification need be made to the pole surfaces themselves, and in that the fixture can be positioned at any desired location relative to the pole axis. However, it is also possible to provide the pole surfaces or other portions of the static field magnet structure with attachment points interengageable with the a fixture. For example, the pole surfaces of the magnet can be provided with a plates 300 having an array of holes 304. Only one such plate being visible in FIG. 6; the plate on the opposite pole (not shown) is identical. The plates on both poles have holes disposed at the same locations relative to the polar axis 360. A patient support in the form of an elongated rod 310 can be positioned within any hole 304 of plate 300 and within the corresponding hole of the opposite plate. Rod 310 can include two sections 312 and 314, section 314 being telescopically received in section 312 to facilitate positioning of the rod. However, the requirement for special plates 300 and 302 constitutes a drawback of this embodiment; these plates consume valuable space between the poles, and reduce the room available to the patient. Moreover, the support can only be positioned at locations where holes are provided.

In the embodiments discussed above, the fixture is used in conjunction with a magnet having a horizontal polar axis. However, the fixture may be used in conjunction with other forms of magnetic resonance imaging apparatus as well. For example, the fixture can be used with a magnet having a vertical pole axis. This may be advantageous in positioning of limbs, joints, and other body parts for imaging.

In the embodiment discussed above with reference to FIG. 1, the cradle 131 and safety switch 129 act to determine whether the fixture 150 is in an active position within the patient-receiving space. If the fixture 150 is in the cradle, it is outside of the patient-receiving space and actuator 122 is enabled. If the fixture 150 is not in the cradle, switch 129 is open and the system assumes that fixture 150 is in an active position; in this condition, actuator 122 is disabled. Where a plurality of fixtures 150 are provided as, for example, in the embodiment of FIG. 4, the system may include a plurality of cradles, equal in number to the number of fixtures, and a plurality of safety switches connected in series or otherwise connected so that all of the fixtures must be present in all of the cradles to enable the actuator. Also, an operator-perceptible signal can be provided to indicate whether all of the fixtures are in their cradles as, for example, by a lamp or LED connected to the safety switches so that the lamp or LED illuminates only when all of the switches are closed.

Other devices capable of detecting whether or not a fixture is in an active position can be used in similar fashion. For example, each fixture may be equipped with one or more pressure-sensitive switches linked to the pads so that whenever the pads are pressed against the pole faces the switches are in one condition, whereas when the pads are released from engagement the switches are in the opposite condition. Alternatively, each fixture may be provided with a magnetic field sensor. A high reading from the field sensor indicates that the fixture is disposed within the patient-receiving space, whereas a low reading indicates that the fixture is outside of the patient-receiving space. Optical or sonic devices mounted to the fixture and/or to the magnet also can be used to determine whether or not the fixture is in an active position within the patient-receiving space.

Alternately or additionally, the fixture can be equipped with devices for detecting proximity of a patient to the rest or contact of a patient with the rest and disabling the actuator when such proximity or contact is detected. This arrangement prevents pinching of the patient, and allows movement of the patient support while the fixture remains in place. However, it requires that the actuator be capable of stopping movement of the patient support promptly when proximity or contact is detected. In a variant of this approach, the actuator can be arranged to reverse movement of the patient support if proximity or contact is detected, so as to move the patient away from the fixture. In one example of a contact detector, a fixture is covered by a shell resiliently mounted to the rest so that the shell can be displaced transverse to the axis of the fixture. A switch is in one condition when the shell is in a normal position relative to the fixture and in an opposite condition when the shell is displaced from this normal position. The actuator is disabled when the shell is displaced. An optical proximity detector can be arranged to pass a light beam from a source to a photocell along a path which extends alongside the rest. Proximity of the patient to the rest causes interruption of the light beam, and a change in the signal from the photocell. The actuator is disabled in response to this change. Other known proximity detectors, including capacitive, pneumatic, optical devices, can be used in the same way.

The fixtures and safety arrangements described above are particularly useful in MRI scanners. However, the fixtures and safety arrangements also can be employed in other imaging apparatus as, X-RAY, CAT, PET apparatus.

Figure 7:
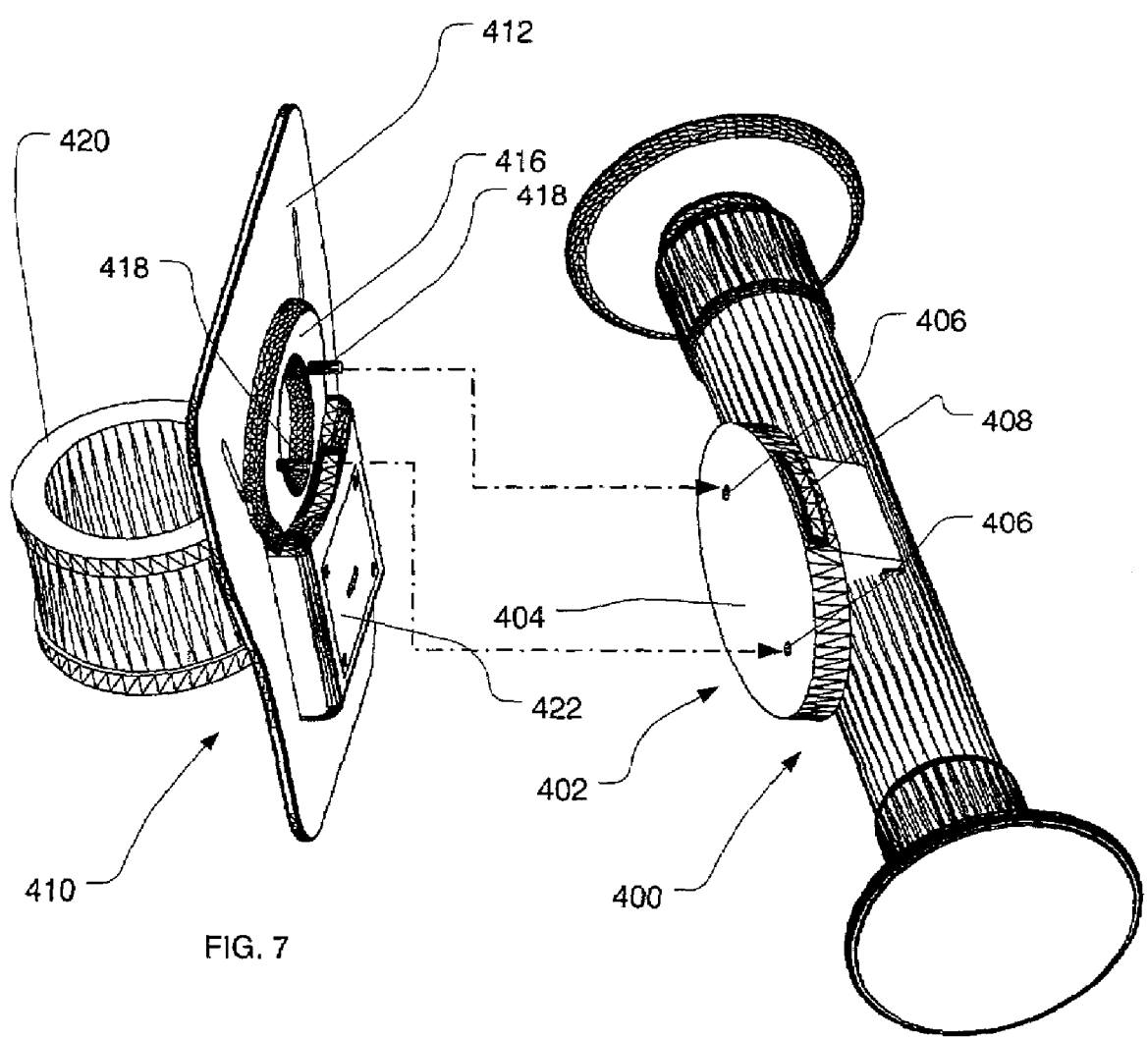
FIG. 7 is an exploded view depicting apparatus in accordance with another embodiment of the invention.

The fixture can be used for supporting structures other than a portion of the patient's body. For example, as seen in FIG. 7, the fixture 400 generally similar to the fixture shown in FIG. 5 is provided with a fitting 402 incorporating a platform 404 facing generally transverse to the axis of the fixture. Platform 404 has a pair of holes 406. A releasable latch mechanism (not shown) is provided within platform 404. A button 408 is connected to the releasable latch mechanism.

A local coil assembly 410 incorporates a plate 412 having a pad 416 projecting from one surface. A pair of pins 418 extend from pad 416. A small loop coil antenna 420 is mounted on the side of plate 412 opposite from pad 416. Other, ancillary devices such as capacitors and/or electrical connectors adapted to function with coil 420 are also mounted to plate 412 as, for example, in a housing 422. Coil assembly 410 can be releasably mounted on fixture 400 by engaging pins 418 in holes 406. The latch within platform 404 holds the pins in the holes and holds pad 416 in engagement with the surface of platform 404. Thus, the coil assembly can be fixed in essentially any desired position by installing the patient rest between the poles and engaging the coil assembly with the fixture either before or after installing the fixture in the patient-receiving space.

Because the coil assembly can be positioned at essentially any location within the patient-receiving space, this adds further versatility. In a similar manner, other devices used or useful in the environment of an MRI scanner can be fixed in position within the patient-receiving space. For example, life support equipment such as intravenous solution containers or hoses for supplying oxygen to a patient can be mounted essentially anywhere within the patient-receiving space of the static field magnet.

As these and other variations and combinations can be employed, the foregoing description of the preferred embodiments should be taken by way of illustration rather than by way of limitation of the invention as defined by the claims.

The invention claimed is:

1. A magnetic resonance imaging system; comprising:
   a magnetic resonance imaging apparatus having a first pole face and a second pole face disposed opposite the said first pole face; and
   a fixture comprising:
   (a) a structure;
   (b) first and second pads connected to said structure, said first and second pads being movable between a collapsed condition in which said pads are disposed at a first distance from one another and an expanded condition in which said pads are at a second distance from one another greater than said first distance, said structure being disposed between said first and second pole faces such that said first and second pads engage said first and second pole faces of the imaging apparatus and secure said structure to said first and second pole faces when said pads are in said expanded condition.

2. A system as claimed in claim 1 wherein said structure includes a structural element which is substantially in the form of an elongated rod extending between said pads at least when said pads are in said expanded condition.

3. A system as claimed in claim 2, wherein at least one of said pads is pivotally connected to said structural element for pivoting movement about at least one pad pivot axis transverse to the direction of elongation of said structural element.

4. A system as claimed in claim 3, wherein said first pad and said second pad include planar surfaces adapted to bear on said pole faces.

5. A system as claimed in claim 2 wherein said structural element includes a first elongated section coupled to said first pad, a second elongated section coupled to said second pad, and a connector connecting said sections so that said sections are movable relative to one another to move the pads between said collapsed and expanded conditions.

6. A system as claimed in claim 5, wherein said connector includes a hinge allowing pivoting movement of said first and said second sections about a hinge pivot axis in a first direction from a folded position in which said elongated sections are not collinear and an unfolded position in which said elongated sections are substantially collinear, and a stop limiting pivoting movement in said first direction beyond said unfolded position.

7. A system as claimed in claim 6, wherein said first pad is adjustably connected to said first section so that said first pad can be adjusted relative to said first section in the direction of elongation of said first section.

8. A system as claimed in claim 6, further comprising a locking mechanism for locking said first and second sections in said unfolded position.

9. A system as claimed in claim 5, further comprising a screwjack, said first pad being connected to said first section through said screwjack, said screwjack providing an adjustable connection.

10. A system as claimed in claim 2, wherein said structural element includes a first elongated section and a second section slidably movable relative said first section between a retracted position and an extended position.

11. A system as claimed in claim 10, further comprising a locking mechanism for holding said second section in said extended position.

12. In combination, a magnetic resonance imaging apparatus comprising:
   (a) a static field magnet having a first pole face and a second pole face opposed and spaced apart from one another and defining a patient-receiving space between said pole faces;
   (b) a patient support for supporting a patient within said patient-receiving space; and
   (c) a fixture comprising a structure and first and second pads connected to said structure, said first and second pads being movable between a collapsed condition in which said pads are disposed at a first distance from one another and an expanded condition in which said pads are at a second distance from one another greater than said first distance, said structure being disposed between said first and second pole faces such that said first and second pads engage said first and second pole faces of the imaging apparatus and secure said structure to said first and second pole faces when said pads are in said expanded condition.

13. The combination as claimed in claim 12 wherein said pole faces extend substantially vertically and are spaced apart from one another in a horizontal direction, and wherein said patient support is operative to pivot the patient about a substantially horizontal patient pivot axis.

14. Imaging apparatus comprising:
   (a) an imaging unit defining a patient-receiving space;
   (b) a patient support;

(c) an actuator operative to move the patient support, with the patient thereon, within the patient-receiving space;

(d) a fixture removably mountable within the patient-receiving space by frictionally engaging the fixture to a structure that forms a portion of the imaging unit;

(e) a detector connected to the fixture, said detector being arranged to disable the actuator when the fixture is mounted in an active position within said patient-receiving space; and (f) a cradle disposed outside of said patient-receiving space, said detector including a safety switch mounted in proximity to said cradle so that said safety switch is in a first condition and said actuator is enabled when said fixture is disposed in said cradle and said safety switch is in a second condition and said actuator is disabled when said fixture is not in said cradle.

* * * * *

UNITED STATES PATENT AND TRADEMARK OFFICE
CERTIFICATE OF CORRECTION

PATENT NO.       : 7,239,906 B1  
APPLICATION NO.  : 10/126015  
DATED            : July 3, 2007  
INVENTOR(S)      : Charles A. Green et al.

Page 1 of 1

It is certified that error appears in the above-identified patent and that said Letters Patent is hereby corrected as shown below:

Title page item [54] and Column 1, Title, "MAGNETIC RESONANCE IMAGING SYSTEM INCLUDING A TRANSPOLAR FIXTURE" should read -- TRANSPOLAR FIXTURE FOR AN IMAGING APPARATUS --.

Signed and Sealed this

Eighth Day of July, 2008

JON W. DUDAS  
*Director of the United States Patent and Trademark Office*